United States Patent [19]

Carter et al.

[11] 4,214,475

[45] Jul. 29, 1980

[54] ADAPTER FOR A SENSITIVE VISCOMETER

[75] Inventors: Walter H. Carter, Houston, Tex.; Charles A. Christopher, Broken Arrow, Okla.; Karl-Heinz Grodde, Celle, Fed. Rep. of Germany

[73] Assignees: Texaco Inc., White Plains, N.Y.; Deutsche Texaco Aktiengesellschaft, Hamburg, Fed. Rep. of Germany

[21] Appl. No.: 920,940

[22] Filed: Jun. 30, 1978

[51] Int. Cl.$^2$ .................................. G01N 11/14
[52] U.S. Cl. .................................................. 73/59
[58] Field of Search .................................... 73/59, 60

[56] References Cited

U.S. PATENT DOCUMENTS

| | | | |
|---|---|---|---|
| 2,096,222 | 10/1937 | Bock | 73/59 |
| 2,120,351 | 6/1938 | Decker | 73/59 |
| 2,828,621 | 4/1958 | Von Rosenberg | 73/59 |
| 3,053,078 | 9/1962 | Jewett | 73/59 X |
| 3,456,494 | 7/1969 | Zimmer | 73/60 |
| 3,803,903 | 4/1974 | Lin | 73/59 |

FOREIGN PATENT DOCUMENTS

| | | | |
|---|---|---|---|
| 844362 | 7/1952 | Fed. Rep. of Germany | 73/59 |
| 1078351 | 3/1960 | Fed. Rep. of Germany | 73/59 |
| 137306 | 7/1960 | U.S.S.R. | 73/60 |
| 586369 | 12/1977 | U.S.S.R. | |

OTHER PUBLICATIONS

Zhukov, V. G. *Bell-Type Measuring Attachment for RV-8 Viscometer*, Ind. Lab. vol. 38, No. 10, p. 1629, Oct. 1972.

*Primary Examiner*—Gerald Goldberg
*Assistant Examiner*—Joseph W. Roskos
*Attorney, Agent, or Firm*—Carl G. Ries; Robert A. Kulason; Henry C. Dearborn

[57] ABSTRACT

An adapter for a sensitive viscometer. It provides increased drag at low shear rates to increase the accuracy. There is an inverted cup shaped rotor that cooperates with an annular shaped stationary container for the fluid to be measured. The annular shape of the container provides reaction surfaces with the fluid on both the inner and outer surfaces of the rotor. And, there is a reservoir in the stationary container with an overflow edge, so that the quantity of fluid to be measured is accurately metered.

8 Claims, 3 Drawing Figures

U.S. Patent  Jul. 29, 1980  4,214,475
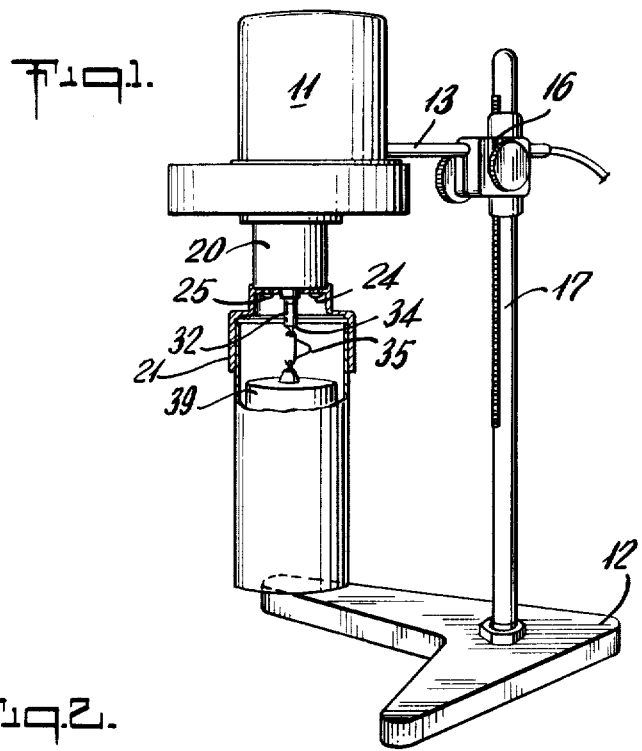
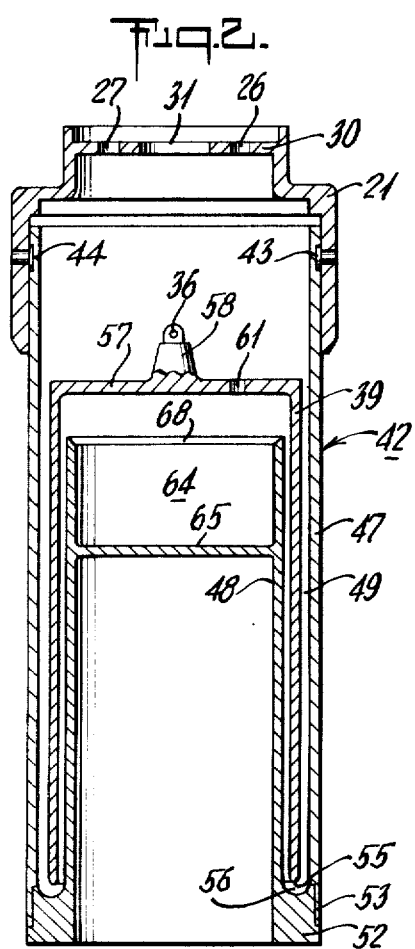
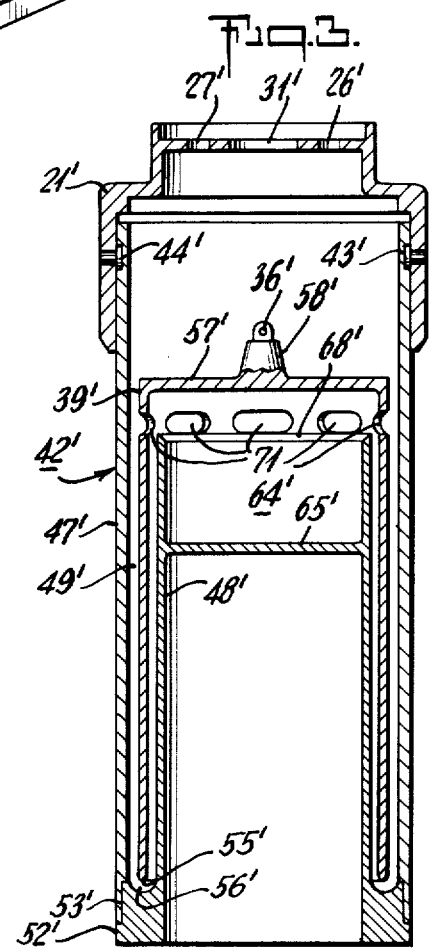

ADAPTER FOR A SENSITIVE VISCOMETER

BACKGROUND OF THE INVENTION

1. Field of the Invention

This invention concerns viscometers, in general, and more specifically relates to an adapter for use with a sensitive type of viscometer.

2. Description of the Prior Art

In connection with petroleum reservior studies, it has been found that there is a need for being able to measure the viscosity of low viscosity solutions, at shear rates that are to be expected in actual reservoirs. Such shear rates are on the order of less than ten reciprocal seconds, and the low viscosity of interest is on the order of less than ten centipoise.

Heretofore, the only known instrument, or type of instrument, available for making satisfactory measurements in the indicated range of viscosity has been a Weissenburg Rheogoniometer. However, such an instrument is extremely costly and is hard to operate. On the other hand, there is an inexpensive viscometer that is commercially available and manufactured by Brookfield Engineering Laboratories, Inc. of Stoughton, Mass. 02072. The latter, however, is incapable of making accurate measurements in the low shear rate range desired. Furthermore, no known prior patent, e.g. U.S. Pat. No. 2,096,222 to G. E. Bock, Oct. 19, 1937, nor the commercial structure suggested by Brookfield in connection with its model LV Synchro-Lectric Viscometers have suggested structure for an adapter that has the desired capabilities.

Consequently, it is an object of this invention to teach a novel and mertiorous structure for an adapter that can be used with a commercial viscometer in order to provide for making accurate low shear rate measurements of fluids having low viscosity. Such adapter providing capability of accurate measurements comparable to those of a complicated Rheogoniometer.

SUMMARY OF THE INVENTION

Briefly, the invention is related to a rheometer for measuring viscosity at low shear rates. In such an instrument it concerns an improved adapter for a sensitive viscometer. Such adapter comprises a stationary container for holding a predetermined quantity of fluid to be measured, and an inverted cup shaped rotor for cooperating with said container and fluid to create drag related to said viscosity. The said stationary container has an annular shape for providing reaction drag on the both inner and outer surfaces of said rotor, and the said stationary container also has means for metering the effective quantity of said fluid to be measured.

Again briefly, in connection with a rheometer for measuring low viscosity at low shear rates, the invention concerns an improved adapter for a sensitive viscometer, which comprises a stationary container for holding a predetermined quantity of fluid to be measured. Such stationary container comprises an outer cylindrical wall having means for attaching it to said sensitive viscometer, and a coaxial inner cylinder forming an annular space between the inside of said outer cylindrical wall and the outside of said inner cylinder. The stationary container also comprises a smoothly rounded surface joining said coaxial inner cylinder with said outer cylindrical wall at the bottom to reduce eddy currents in said fluid. The improved adapter also comprises an inverted cup shaped cylindrical rotor for cooperating with said annular space and said fluid therein to create drag related to said viscosity. Such cylindrical rotor comprises a hollow closed top cylinder having a diameter and wall thickness adapted for free rotation in said annular space, and an opening in said top for equalizing the pressure on said fluid when the rotor is in place for measuring viscosity. The improved adapter also comprises means integral with said stationary container for metering the effective quantity of said fluid to be measured. Such integral means comprises an open topped reservoir integral with the upper portion of said coaxial inner cylinder and having sufficient volume to receive overflow of said fluid when said rotor is in place for measuring viscosity.

BRIEF DESCRIPTION OF THE DRAWINGS

The foregoing and other objects and benefits of the invention will be more fully set forth below in connection with the best mode contemplated by the inventors of carrying out the invention, and in connection with which there are illustrations provided in the drawings, wherein:

FIG. 1 is a perspective with a partial cutaway in cross section illustrating a viscometer instrument mounted for use on a stand, and having an adapter connected thereto;

FIG. 2 is a somewhat enlarged cross section showing an adapter according to the invention; and FIG. 3 is a cross section like FIG. 2 illustrating a modification according to the invention.

DESCRIPTION OF THE PREFERRED EMBODIMENTS

The invention relates to a rheometer of the type that can measure low viscosity at low shear rates. And, it concerns an improved adapter for a sensitive type of viscometer. The adapter is such that the capabilities of a thrifty sensitive viscometer are improved sufficiently to obtain desired accuracy at the indicated low viscosity and low shear rates. Such information is valuable in connection with petroleum reservoir studies, and in addition there are other fields where this type of information is of value such as in ink manufactures and the like.

While the particular modifications of an adapter in accordance with this invention are designed for application and use with a particular viscometer that is commercially available, it will be clear to anyone skilled in the art that the principals involved in an adapter according to the invention might be applied to other and different viscometers. FIG. 1 illustrates a commercial type viscometer 11 that is mounted on a stand 12 by an arm 13 that extends horizontally and is held by a clamp 16. The clamp 16 may be vertically adjustable in its location vertically along an upright support post 17.

The viscometer 11 includes a pivot housing 20 to which an adapter body 21 is attached in any feasible manner, e.g. by means of the illustrated rivet heads 24 and 25 that cooperate with a corresponding pair of key hole shaped openings 26 and 27 (see FIG. 2) respectively. These openings are situated in an upper surface 30 inside of the top of the adapter body 21. This surface 30 only extends radially inward far enough to accomodate the key hole shaped openings 26 and 27. It has a large opening or centrally located hole 31 for accomodating a shaft 32 that is rotated by the viscometer 11.

It will be understood that the viscometer 11 acts to drive the shaft 32 in rotation while measuring the torque or drag that is reflected at said shaft by any resistance to such rotation coming from the viscometer attachments. Such rotation is transmitted from the shaft 32 via any feasible coupling, e.g. a double hook 35. The top of hook 35 hooks into an eye 34 at the bottom of shaft 32, and the bottom of the hook 35 hooks into a similar eye 36 (see FIG. 2) which is located at the top of a rotor 39.

It may be noted that the stand 12 is preferably made adjustable (not shown) so that the adapter body 21 and related parts will be situated in a true vertical position. Also, it will be appreciated that the body 21 of the adapter is made so as to accomodate and support the remaining parts of the adapter. This may be done by means of various feasible arrangements. The construction illustrated is merely an example of a type of structure that is directly applicable to a Brookfield type viscometer.

FIGS. 2 and 3 are two different modifications of the structure of an adapter according to the invention. Referring to FIG. 2, it will be observed that the adapter body 21 supports a stationary container 42 that will hold a predetermined quantity of fluid to be measured. In the illustrated arrangement, the container 42 is attached to the inside of the body 21 by having vertical grooves (not shown) to accomodate a pair of rivet heads 43 and 44. Then after the container 42 has been thus inserted upward into the body 21, with the indicated grooves aligned with the rivet heads 43 and 44, the container 42 will be rotated a short distance in either direction. This will hold it in place because there is a groove (not shown) that runs horizontally around the periphery of the container having a width that will accomodate the rivet heads.

The container 42 is made up of three major parts. A first of these is an outer cylindrical wall 47 that contains the above described grooves for attaching the upper portion to the body 21 of the whole adapter. The adapter, in turn, attaches to the viscometer 11, as indicated above.

The container 42 also has a coaxial inner cylinder 48 that forms an annular space 49 between the inside of the outer cylindrical wall 47 and the inner cylinder 48. These two cylinders 48 and 47 are integrally attached together in any feasible manner. For example, there is a solid bottom ring 52 which is an integral part of the cylinder 48 with a fluid tight joint 53 for connecting it to the outer cylinderical wall 47.

There is a smoothly rounded surface 56 that is formed in the top edge of the ring 52. This acts to reduce eddy currents in the fluid being measured which might occur at the bottom edge of the rotor 39. Similarly, the bottom edge 55 of the rotor 39 is preferably rounded to complement the rounded surface 56.

Rotor 39 is constructed like an inverted cup shaped cylinder which is hollow with a closed top 57. There is a hub 58 which is molded to the top 57 and to which is attached the eye 36. It is to be noted that the rotor cylinder 39 is constructed with a wall thickness adapted for permitting free rotation in the annular space 49 formed by the two walls 47 and 48 of the stationary container 42.

There is an opening or port 61 in the top 57 of the rotor 39. This is provided in order to equalize the pressure on the fluid (not shown) when it is in the container 42 to have the viscosity measured. Consequently, when the fluid is introduced into the annular space 49, it will be self leveling between the outside and inside of the cylinder i.e. rotor 39. This will be explained more fully below.

An important feature of the invention is the ability to meter the effective quantity of the fluid to be measured. This is accomplished by having a reservoir 64 that is integral part of the coaxial inner cylinder 48. The reservoir 64 is formed by a partion, of floor 65 which extends transversely across the cylinder 48 at an appropriate distance beneath the top edge thereof. There is an inwardly beveled edge 68 at the top of the cylinder 48, and this acts to meter the level of the fluid by allowing any excess to flow down into the reservoir 64. This provides an automatic self leveling, and quantity measuring arrangement for the fluid being measured for viscosity.

FIG. 3 is another modification of the adapter structure according to the invention. Most of the elements are substantially the same as those illustrated in FIG. 2 so that the corresponding reference numbers with primed marks will be employed and these elements need not be described again here. Thus, the only difference is in the rotor 39' which does not have any opening in the horizontal portion of the top 57'. Rather, it has a plurality of openings 71 that may be somewhat elongated circumferentially as indicated. They are preferrably so situated that the bottom edges thereof will be horizontally aligned with the top edge of the beveled edge 68' when the rotor is in place in the adapter and ready for making a viscosity measurement. This permits a rapid action of leveling the fluid as the metering takes place by the action of the flow of the fluid over the edge 68' into the reservoir 64'.

While particular embodiments of the invention have been described in considerable detail in accordance with the applicable statutes, this is not to be taken as in any way limiting the invention but merely as being descriptive thereof.

We claim:

1. In a rheometer for measuring low viscosities at low shear rates, an improved adapter for a sensitive viscometer, comprising a cylindrical stationary container for holding a predetermined quantity of fluid to be measured, and a cylindrical inverted cup shaped rotor adapted for free rotation within said stationary container and for cooperating with said container and fluid to create drag related to said viscosity, said stationary container having an annular shape comprising a coaxial inner cylinder having an outside diameter less than the inside diameter of said rotor and a smoothly rounded surface joining it with said stationary cylindrical container at the bottom to reduce eddy currents in said fluid, said stationary container annular shape providing reaction surfaces on both the inner and outer surfaces of said rotor, said stationary container also having a reservoir for receiving overflow of said fluid above a predetermined level within said rotor for metering the effective quantity of said fluid to be measured, and said cylindrical rotor having a rounded bottom edge to complement said smoothly rounded surface.

2. An improved adapter according to claim 1, wherein said metering reservoir is incorporated in said stationary inner cylinder.

3. An improved adapter according to claim 2, wherein
said metering reservoir comprises a hollow space at the top of said stationary inner cylinder to receive overflow of said fluid when said rotor is in place for measuring viscosity.

4. An improved adapter according to claim 3, wherein
said cylindrical rotor is hollow and includes means for equalizing the pressure on said fluid when the rotor is in place for measuring viscosity.

5. An improved adapter according to claim 4, wherein
said pressure equalizing means comprises an opening in the top of said rotor above the level of said metering reservoir ingress.

6. An improved adapter according to claim 5, wherein
said cylindrical rotor has a closed top, and
said opening in the rotor top comprises a port therein for free passage of gas therethrough.

7. An improved adapter according to claim 6, wherein
said opening in the rotor top comprises a plurality of openings spaced circumferentially around the top and having the bottom edges thereof located at the same level as said metering reservoir ingress when the rotor is in place for measuring viscosity.

8. In a rheometer for measuring low viscosities at low shear rates, an improved adapter for a sensitive viscometer, comprising (1) a stationary container for holding a predetermined quantity of fluid to be measured, comprising
  (a) an outer cylindrical wall having means for attaching it to said sensitive viscometer,
  (b) a coaxial inner cylinder forming an annular space between the inside of said outer cylindrical wall and the outside of said inner cylinder, and
  (c) a smoothly rounded surface joining said coaxial inner cylinder with said outer cylindrical wall at the bottom to reduce eddy currents in said fluid,
(2) an inverted cup shapped cylindrical rotor for cooperating with said annular space and said fluid therein to create drag related to said viscosity, comprising
  (a) a hollow closed top cylinder having a diameter and wall thickness adapted for free rotation in said annular space,
  (b) an opening in said top for equalizing the pressure on said fluid when the rotor is in place for measuring viscosity, and
  (c) a rounded bottom edge to complement said smoothly rounded surface, and
(3) means integral with said stationary container for metering the effective quantity of said fluid to be measured, comprising
  (a) an open topped reservoir integral with the upper portion of said coaxial inner cylinder and having sufficient volume to receive overflow of said fluid when said rotor is in place for measuring viscosity.

* * * * *